United States Patent
Kamei et al.

(10) Patent No.: US 7,285,290 B2
(45) Date of Patent: Oct. 23, 2007

(54) HYDROPHILIZED POWDER AND A COMPOSITION COMPRISING THE SAME

(75) Inventors: Masanao Kamei, Gunma (JP); Kiyomi Tachibana, Tokyo (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 141 days.

(21) Appl. No.: 10/701,566

(22) Filed: Nov. 6, 2003

(65) Prior Publication Data

US 2004/0091440 A1 May 13, 2004

(30) Foreign Application Priority Data

Nov. 8, 2002 (JP) .............................. 2002-324840

(51) Int. Cl.
*A61K 9/66* (2006.01)
*A61K 33/24* (2006.01)
*A61K 33/30* (2006.01)
*A61K 31/695* (2006.01)
*A61K 31/28* (2006.01)
*A61K 31/315* (2006.01)
*A61Q 1/10* (2006.01)
*A01N 59/16* (2006.01)
*A01N 55/02* (2006.01)

(52) U.S. Cl. .................. 424/489; 424/70.12; 424/455; 424/617; 424/641; 514/63; 514/492; 514/494

(58) Field of Classification Search ................ 424/401, 424/59, 60, 65, 67, 70.7, 70.9, 70.12, 78.02, 424/78.03, 489, 641, 455, 617; 514/492, 514/494, 63

See application file for complete search history.

(56) References Cited

U.S. PATENT DOCUMENTS 6,660,281 B1 * 12/2003 Nakanishi et al. ........... 424/401
2002/0114771 A1 * 8/2002 Nakanishi ................. 424/70.12
2002/0131947 A1 * 9/2002 Nakanishi ................. 424/70.12
2004/0091440 A1 * 5/2004 Kamei et al. ............. 424/70.12

FOREIGN PATENT DOCUMENTS

| EP | 0 699 721 A2 | 3/1996 |
| EP | 1 123 697 A1 | 8/2001 |
| EP | 1 352 625 A1 | 10/2003 |
| JP | 7-207187 A | 8/1995 |
| JP | 09-104833 A | 4/1997 |
| JP | 1065234 A2 * | 1/2001 |

OTHER PUBLICATIONS

Machine Translation of Takeshi et al. JP 09-104833 Apr. 22, 1997.*

* cited by examiner

*Primary Examiner*—Johann Richter
*Assistant Examiner*—Ernst Arnold
(74) *Attorney, Agent, or Firm*—Birch, Stewart, Kolasch & Birch, LLP

(57) ABSTRACT

The present invention is hydrophilized powder, wherein the powder is surface treated with polyether-modified silicone having a hydrolyzable silyl group according to the formula (1), $$R^1_a R^2_b R^3_c SiO_{(4-a-b-c)/2} \quad (1)$$

wherein $R^1$ is an organic group having 1 to 80 carbon atoms, $R^2$ is a polyether group according to the following formula (2), $$-C_d H_{2d} - O - (C_2 H_4 O)_e (C_3 H_6 O)_f R^4 \quad (2)$$

wherein d, e, and f are integers with $0 \leq d \leq 15$, $1 \leq e \leq 50$, and $0 \leq f \leq 50$,
$R^3$ is a silyl group having a hydrolyzable group according to the general formula (3), $$-C_d H_{2d} - SiR^1_g (OR^5)_{3-g} \quad (3)$$

wherein d is as define above and $0 \leq g \leq 2$, and $0.5 \leq a \leq 2.5$, $0.1 \leq b \leq 1.5$, and $0.01 \leq c \leq 1.5$. The invention also provides a composition comprising the powder, an aqueous dispersion comprising the powder, and their application in cosmetics, coatings, and inks.

13 Claims, No Drawings

HYDROPHILIZED POWDER AND A COMPOSITION COMPRISING THE SAME

CROSS REFERENCE

This application claims benefit of Japanese Patent application No. 2002-324840 filed on Nov. 8, 2002, the contents of which are hereby incorporated by reference.

FIELD OF THE INVENTION

The present invention relates to new hydrophilized powder which is surface-treated with new polyether-modified silicone having a hydrolyzable group, a composition comprising the same, an aqueous dispersion comprising the same, and their application in cosmetics, coatings, and inks.

Untreated powder aggregates easily due to charge or polarity on the powder surface and to a small amount of impurity. In order to solve this problem and to thereby improve dispersibility and stability of powder, surface treatments with various treating agents were proposed.

Agents and methods for surface treating powder vary depending on the aim of the treatment. A treating agent may be selected in view of properties of the surface to be treated and its interaction with a dispersion medium. Known methods include, for instance, lipophilizing treatment with oils or metal soaps, hydrophilizing treatment with surfactants or water-soluble polymers, and water-repellent or oil-repellent treatment with silicone oils.

However, in conventional lipophilizing treatments, surfactants or water-soluble polymer of the prior art are not satisfactory. For instance, in a composition formulated with the treated powder the treating agent separates from the powder to cause aggregation of the powder. This results in mottles and color difference between a coating color and a resultant color, In addition, re-dispersibility sometimes worsens, which is very much inconvenient in its use. Further, some surfactant used in the prior art cause skin irritation, which is problematic in cosmetics.

SUMMARY OF THE INVENTION

The object of the present invention is to provide hydrophilized powder which is sufficiently hydrophilic, does not aggregate easily, has good dispersibility, and does not cause skin irritations, and a composition comprising the same.

The inventors have made intensive studies on hydrophilization of powder to achieve good dispersibility and good stability of a dispersion of the powder and have found that the object can be accomplished by using hydrophilized powder which is surface-treated with polyether-modified silicone having a hydrolyzable silyl group.

DESCRIPTION OF THE PREFERRED EMBODIMENTS

Polyether-modified silicone having a hydrolyzable silyl group that is used in the present invention is represented by the following formula (1).

$$R^1_a R^2_b R^3_c SiO_{(4-a-b-c)/2} \tag{1}$$

Examples of $R^1$ include alkyl groups such as a methyl group, an ethyl group, a propyl group, a butyl group, a pentyl group, a hexyl group, a heptyl group, a octyl group, a nonyl group, and a decyl group; cycloalkyl groups such as a cyclopentyl group and a cyclohexyl group; aryl groups such as a phenyl group and a tolyl group; aralkyl groups such as a benzyl group and a phenetyl group; and fluorinated alkyl groups such as a trifluoropropyl group and a heptadecafluorodecyl group.

$R^2$ is a polyether group according to the following general formula (2).

$$-C_d H_{2d}-O-(C_2H_4O)_e(C_3H_6O)_f R^4 \tag{2}$$

$R^4$ is a hydrogen atom or an alkyl group such as a methyl group, an ethyl group, and a propyl group and d, e, and f are integers with $0 \leq d \leq 15$, $1 \leq e \leq 50$, and $0 \leq f \leq 50$.

$R^3$ is a hydrolyzable silyl group according to the following general formula (3)

$$-C_d H_{2d}-SiR^1_g(OR^5)_{3-g} \tag{3}$$

$R^1$ has the same meaning as defined above and $R^5$ is a hydrogen atom or an alkyl group such as a methyl group, an ethyl group, and a propyl group. The letter "d" has the same meaning as defined above, g is an integer with $0 \leq g \leq 2$, and $0.5 \leq a \leq 2.5$, preferably $1.0 \leq a \leq 2.0$, $0.1 \leq b \leq 1.5$, preferably $0.3 \leq b \leq 1.0$, and $0.01 \leq c \leq 1.5$, preferably, $0.1 \leq c \leq 1.0$.

When the silicone according to the above formula (1) is used as the surface treating agent for powder, the weight average molecular weight of the silicone is preferably 300 to 100,000, but not limited to these. The content of the polyether moiety is preferably 30 to 90%, and more preferably 60 to 80%, relative to the total molecular weight.

One embodiment of the present invention is a hydrophilized powder, wherein the powder is surface treated with a polyether-modified silicone having a weight average molecular weight of from 300 to 100,000 and a hydrolyzable silyl group according to the formula $R^1_a R^2_b R^3_c SiO_{(4-a-b-c)/2}$ wherein $0.5 \leq a \leq 2.5$, $0.1 \leq b \leq 1.0$, and $0.01 \leq c \leq 1.0$, and $R^1$ may be same with or different from each other and is an organic group selected from the group consisting of $C_{1-30}$ alkyl groups, aryl groups, aralkyl groups, and fluorinated alkyl groups, $R^2$ is a polyether group according to the following formula $-C_d H_{2d}-O-(C_2H_4O)_e R^4$ wherein $R^4$ is a $C_{1-30}$ alkyl group and d and e are integers with $0 \leq d \leq 15$ and $1 \leq e \leq 50$, a content of the polyether moiety $(C_2H_4O)_e$ ranging from 50 to 80 weight-% relative to the weight of the polyether-modified silicone, and $R^3$ is a silyl group having a hydrolyzable group according to the formula $-C_d H_{2d}-SiR^1_g (OR^5)_{3-g}$ wherein $R^1$ is as defined above, $R^5$ is a hydrogen atom or a $C_{1-6}$ alkyl group, d is as defined above, and $0 \leq g \leq 2$.

The silicone compound according to the above formula (1) can be easily prepared by an addition reaction of organohydrogenpolysiloxane with polyether having unsaturation at one end and with hydrolyzable silane having unsaturation in the presence of platinum catalyst or rhodium catalyst.

Examples of the hydrolyzable silane having unsaturation include the following, but are not limited thereto.

$CH_2=CHSi(OCH_3)_3$ $CH_2=CHSi(OC_2H_5)_3$ $CH_2=CHSiCH_3(OCH_3)_2$ $CH_2=CHC_6H_{12}Si(OC_2H_5)_3$ $CH_2=CHC_6H_{12}Si(CH_3)_2(OC_2H_5)$

The organohydrogenpolysiloxane herein may be linear, cyclic or branched. The bonding site of the SiH group is not particularly limited but may be at a side chain or a terminal group.

The above-described addition reaction is preferably carried out in the presence of platinum catalyst or rhodium catalyst. Specifically suitable catalyst includes chloroplatinic acid, alcohol-modified chloroplatinic acid and chloroplatinic acid-vinylsiloxane complex. The catalyst can be used in a conventional catalytic amount, preferably in 50 ppm or less, more preferably 20 ppm or less of the amount of platinum or rhodium.

Optionally, the above addition reaction may be carried out in organic solvent as required. Examples of organic solvents include aliphatic alcohols such as methanol, ethanol, 2-propanol and butanol; aromatic hydrocarbons such as toluene and xylene; aliphatic or alicyclic hydrocarbons such as n-pentane, n-hexane and cyclohexane; and halogenated hydrocarbons such as dichloromethane, chloroform and carbon tetrachloride. The conditions of addition reaction are not particularly limited but reaction is preferably performed for 1 to 10 hours under reflux.

Specific examples of powder which can be used in the present invention include inorganic powder, such as titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, higilite, bentonite, montmorillonite, hectolite, zeolite, ceramics powder, calcium secondary phosphate, alumina, aluminum hydroxide, boron nitride, and silica.

Examples of organic powder include polyamide powder, polyester powder, polyethylene powder, polypropylene powder, polystyrene powder, polyurethane powder, benzoguanamine powder, polymethylbenzoguanamine powder, tetrafluoroethylene powder, polymethylmethacrylate powder, cellulose powder, silk powder, nylon powder, Nylon 12, Nylon 6, silicone powder, silicone composite powder, styrene/acrylic acid copolymer, divinylbenzene/styrene copolymer, vinyl resin, urea resin, phenol resin, fluororesin, silicone resin, acrylic resin, melamine resin, epoxy resin, polycarbonate resin, microcryste fiber powder, starch powder, and lauroyl lysine.

Examples of the powder of metal salts of surfactants, i.e. metal soaps, include zinc stearate, aluminum stearate, calcium stearate, magnesium stearate, zinc myristate, magnesium myristate, zinc cetyl phosphate, calcium cetyl phosphate, and zinc sodium cetyl phosphate. Examples of the colored pigments include inorganic red pigments such as iron oxide, iron hydroxide, and iron titanate, inorganic brown pigments such as γ-iron oxide, inorganic yellow pigments such as iron oxide yellow and loess, inorganic black pigments such as iron oxide black and carbon black, inorganic violet pigments such as manganese violet and cobalt violet, inorganic green pigments such as chromium hydroxide, chromium oxide, cobalt oxide, and cobalt titanate, inorganic blue pigments such as Prussian blue and ultramarine blue, lakes of tar pigments, lakes of natural dyes, and composite thereof.

Examples of the pearl pigments include titanium dioxide-coated mica, bismuth oxychloride, titanium dioxide-coated bismuth oxychloride, titanium dioxide-coated talc, fish scales, and titanium dioxide-coated colored mica; metallic powder pigments such as aluminum powder, copper powder and stainless steel powder; tar pigments such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 6, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No, 206, and Orange No. 207; and natural pigments such as carminic acid, laccaic acid, carthamin, brazilin, and crocin.

The powder may be any powder that are commonly used in cosmetics, regardless of the shape, such as spherical, needle or plate, particle diameter such as fume, fine particle, or pigment grade, and particle structure such as porous or non-porous. Composite powders of these powders and/or surface-treated powders with surfactants or water-soluble polymers are also used.

The powder treating agent according to the present invention can be applied on the surface of powder in accordance with any known methods. For instance, a suitable method may be selected from the following methods:

1. a method where the powder surface is treated by dispersing the powder in a medium selected from water or a hydrophilic solvent containing the treatment agent,
2. a method where the surface is treated by mixing the powder and the treatment agent, followed by surface treatment in a mill such as a ball mill and a jet mill, and
3. a method where the treatment agent is sprayed on the powder.

The aqueous dispersion according to the present invention means a dispersion prepared by dispersing the above powder in water and/or a water-soluble oil or a dispersion which is prepared by dissolving or dispersing the water-soluble silicone compound in water, adding powder thereto, and mixing them to disperse. It has a form of a liquid dispersion.

The aqueous dispersion according to the present invention can be prepared in a method selected from, for instance, the following methods:

1. a method where the powder composition obtained as described above is added to water or a hydrophilic oil such as glycol to disperse, and
2. a method where a hydrophilic silicone is dissolved or dispersed in the above-described water soluble oil, in which powder is added and mixed in a mill such as a ball mill, a beads mill or sand mill.

When the silicone of the formula (1) according to the present invention is used as the surface treating agent for powder, 0.1 to 80 parts by weight, preferably 0.5 to 10 parts by weight of the silicone, is used relative to 100 parts by weight of the powder The hydrophilized powder as obtained according to the above-described manner has good dispersibility in an aqueous system and the resulting dispersion has good stability. Therefore, the hydrophilized powder according to the present invention can be applied for various powder compositions, such as cosmetics, external use medicines for skin, coatings, and inks. When the hydrophilized powder according to the present invention is formulated in a composition, the formulation amount has no restriction, but can be in a range of 0.1 to 99.9 wt. %.

In the cosmetic of the present invention, a variety of components that are commonly used in cosmetics can be blended, for example, solid, half solid, or liquid unctuous agents, water, alcohols, water-soluble polymers, film-forming agents, surfactante, oil-soluble gelling agents, water-soluble gelling agents, clay minerals modified with organic compounds, resins, powders, ultraviolet absorbents, moisture retention agents, antiseptics, anti-microbial agents, perfumes, salts, antioxidants, pH regulators, a chelating agents, refreshing agents, anti-inflammatory agents, skin beautifying components, such as skin whitener, cell activator, rough dry skin improver, blood circulation promoter, skin astringent and anti-seborrheic agent, vitamins, amino acids, nucleic acids, hormones, clathrate compounds.

Examples of the above components include the following, but are not limited to those.

Examples of the natural animal or plant oils and semi-synthetic oils which can be used in the cosmetics of the invention include avocado oil, linseed oil, almond oil, Ibota wax, perilla oil, olive oil, cacao butter, kapok wax, kaya oil, carnauba wax, liver oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, camellia kissi seed oil, safflower oil, shear butter, Chinese tung oil, cinnamon oil, jojoba wax, shellac wax, turtle oil, soybean oil, tea seed oil, camellia oil, evening primrose oil, corn oil, lard, rapeseed oil, Japanese tung oil, rice bran oil, germ oil, horse fat, persic oil, palm oil, palm kernel oil, castor oil, hydrogenated castor oil, castor oil fatty acid methyl ester, sunflower oil, grape oil, bayberry wax, jojoba oil, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, isopropyl lanolate, hexyl laurate, POE lanolin alcohol ether, POE lanolin alcohol acetate, lanolin fatty acid polyethylene glycol, POE hydrogenated lanolin alcohol ether, and egg yolk oil.

Examples of the hydrocarbon oils which can be used in the cosmetics of the invention include ozokerite, squalane, squalene, ceresin, paraffin, paraffin wax, liquid paraffin, pristane, polyisobutylene, microcrystalline wax, vaseline and higher fatty acids, e.g., lauric acid, myristic acid, palmitic acid, stearic acid, behenic acid, undecylenic acid, oleic acid, linoleic acid, linoleic acid, arachidonic acid, eicosapentaenoic acid (EPA), docosahexaenoic acid (DHA), isostearic acid, and 12-hydroxystearic acid.

Examples of the higher alcohols which can be used in the cosmetics of the invention include lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alcohol 2-decyltetradecinol, cholesterol, phytosterol, POE cholesterol ether, monostearyl glycerin ether (batyl alcohol, and monooleyl glyceryl ether (cerakyl alcohol).

Examples of the ester oils which can be used in the cosmetics of the invention include diisobutyl adipate, 2-hexyldecyl adipate, di-2-heptylundecyl adipate, N-alkyl glycol monoisostearate, isocetyl isostearate, trimethylolpropane triisostearate, isononyl isononanate, isotridecyl isononanate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprirate, triethyl citrate, 2-ethylhexyl succinate, amyl acetate, ethyl acetate, butyl acetate, isocetyl stearate, butyl stearate, diisopropyl sebacinate, di-2-ethylhexyl sebacinate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldecyl myristate, 2-hexyldecyl myristate, myristyl myristate, hexyldecyl dimethyloctanoate, ethyl laurate, hexyl laurate, 2-octyldodecyl N-lauroyl-L-glutamate, and diisostearyl malate.

Examples of the glyceride oils which can be used in the cosmetics of the invention include acetoglyceryl, glycerol triisooctanoate, glyceryl triisostearate, glyceryl triisopalmitate, glyceryl monostearate, glyceryl di-2-heptylundecanoate, glyceryl trimyristate, and diglyceryl myristate/isostearate.

Examples of the silicone oils which can be used in the cosmetics of the invention include organopolysiloxanes having low or high viscosity, such as dimethylpolysiloxane, methylphenylpolysiloxane, methylhydrogenpolysiloxane and dimethylsiloxane-methylphenylsiloxane copolymer; cyclosiloxanes, such as octamethylcyclotetrasiloxane, decamethylcyclopentasiloxane, dodecamethylcyclohexasiloxane, tetramethyltetrahydrogencyclotetrasiloxane tetramethyl-tetraphenylcyclotetrasiloxane, tetramethyltetratrifluoropropyl cyclotetrasiloxane, and pentamethylpentatrifluoropropylcyclopentasiloxane; silicone rubbers such as gummy dimethylpolysiloxanes and gummy dimethylsiloxaxe/methylphenylsiloxane copolymers having high polymerization degrees; silicone rubber solution in cyclosiloxane; trimethylsiloxysilicate; trimethylsiloxysilicate solution in cyclosiloxane; higher alkoxy-modified silicones such as stearoxy silicones; higher fatty acid-modified silicones; alkyl-modified silicones; amino-modified silicones; and fluorine-modified silicones. Fluorine-containing oils may also be used, such as perfluoropolyether, perfluorodecalin and perfluorooctane.

The cosmetics according to the present invention preferably may comprise one or more compounds having an alcoholic hydroxyl group in the molecular structure, depending on the aim of cosmetics. Examples of compounds having an alcoholic hydroxyl group include lower alcohols such as ethanol and isopropanol; sugar alcohols such as sorbitol and maltose; sterols such as cholesterol, sitosterol, phytosterol, and lanosterol; and polyols such as, butylene glycol propylene glycol, dibuthylene glycol, and pentylene glycol.

Examples of the water-soluble polymers include cellulose polymers such as gum Arabic, tragacanth gum, galactan, locust bean gum, hydroxypropyl cellulose, nitrocellulose, sodium cellulose sulfate, sodium carboxymethyl cellulose, crystalline cellulose, and cellulose powder; alginic acid-derived polymers such as sodium alginate and propylene glycol alginate; vinyl polymers such as polyvinyl methylether, and carboxyvinyl polymer; polyoxyethylene polymers such as polyoxyethylene/polyoxypropylene copolymers; acrylic polymers such as sodium polyacrylate, polyethyl acrylate, and polyacrylamide; other synthetic water-soluble polymers such as polyethyleneimine and cationic polymers; and inorganic water-soluble polymers such as, bentonite, aluminum magnesium silicate, montmorrilonite, beidellite, nontronite, saponite, hectorite, and silicic anhydride. In these water-soluble polymers, film-forming agents, such as polyvinyl alcohol and polyvinyl pyrrolidine are also included.

Examples of the powders are the same as described above and the powder may be any powder that are commonly used in cosmetics, regardless of its shape, such as spherical, needle or plate, particle diameter such as fume, fine particle, or pigment grade, and particle structure such as porous or nonporous.

These powders may be the composite powder or powder which has been treated with general oil, silicone oil other than the silicone oil of the present invention, fluorinated compounds, or surfactants as long as such treatment does not domage the effect of the present invention. One or more of these powders may be used.

One or more surfactants may be used. These surfactants has no particular restriction and may be any surfactants of anionic, cationic, nonionic or amphoteric surfactant, provided that it is commonly used in cosmetics.

Examples of the surfactants are as follows: the anionic surfactants include fatty acid soaps, such as sodium stearate and triethanolamine palmitate, alkylether carboxylic acids and salts thereof, salts of condensates of amino acids with fatty acids, alkyl sulfonate salts, alkenesulfonates, sulfonates of fatty acid esters, fatty acid amide sulfonates, sulfonate sails of the formalin condensates, salts of alkyl sulfates, salts of secondary higher alcohol sulfates, salts of alkyl/allyl ether sulfates, salts of fatty acid ester sulfates, salts of fatty acid alkylolamide sulfates, and salts of Turkey Red oil sulfate, alkyl phosphate salts, ether phosphate salts, alkylallylether phosphate salts, amide phosphate salts, and N-acylamino surfactants.

Examples of the cationic surfactants include amine salts such as alkylamine salts, amine salts of polyamine and amino alcohol fatty acid derivatives, alkyl quaternary ammonium salts, aromatic quaternary ammonium salts, pyridinium salts and imidazolium salts.

Examples of the nonionic surfactants include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ether, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ethers, polyoxyethylene phytosterol ether, polyoxyethylene cholestanol ether, polyoxyethylene cholesteryl ether, linear or branched-polyoxyalkylene-modified organopolysiloxane, linear or branched polyoxyalkylene/alkyl-comodified organopolysiloxane, linear or branched polyglycerin-modified organopolysiloxane, linear or branched polyglycerin-modified organopolysiloxane, linear or branched-polyglycerin/alkyl-comodified organopolysiloxane, alkanolamide, sugar ethers, and sugar amides.

Examples of the amphoteric surfactants include betaine, aminocarboxylates, and imidazoline derivatives.

One or more crossinked organopolysiloxane may be also used, depending upon aim. The crossliniking agent for the crosslinked organopolysiloxane preferably has two or more vinylic reactive sites, which react with hydrogen atoms directly bonded to silicon atoms to form crosslinked structure. Additionally, this crossed organopolysiloxane preferably can absorb a larger amount of oil than that of itself to swell. Examples of the oils include silicone with a low viscosity from 0.65 $mm^2$/sec to 10.0 $mm^2$/sec, hydrocarbon oils and ester oils.

It is also preferred to use a crosslinked organopolysiloxane containing, in the crosslinked molecule, at least a moiety selected from a group consisting of polyoxyalkylene, alkyl, alkenyl, aryl, and fluoroalkyl moieties. Suitable amount of crosslinked organopolysiloxane to be added is preferably 0.1 to 50 wt. %, more preferably 1 to 30 wt. %, based on the total cosmetics.

One or more acrylic/silicone graft or block copolymer resins may be also used, depending on aim. The silicone resin is preferably an acrylic silicone resin containing, in the molecule, at least one moiety selected from a pyrrolidone moiety, a long-chain alkyl moiety, a polyoxyalkylene moiety, and a fluoroalkyl moiety.

Further, one or more dissolved silicone resins with network structure may be also used. The silicone resin with network structure is generally known as MQ resin, MT resin, or MDT resin and is commercially available as dissolved in octamethylcyclotetrasiloxane. It may contain in the molecule at least one moiety selected from a pyrrolidone moiety, a long-chain alkyl moiety, a polyoxyalkylene moiety, a fluoroalkyl moiety, and an amino moiety.

For cosmetics comprising the acrylic/silicone graft or block copolymer and a silicone resin such as the silicone resin with network structure, the amount of silicone resin to be added is preferably 0.1 to 20 wt. %, more preferably 1 to 10 wt. %, based on the total cosmetics.

The oil-soluble gelling agent may be a gelling agent selected from metal soaps, such as aluminum stearate, magnesium stearate and zinc myristate; amino acid derivatives, such as N-lauroyl-L-glutamic acid and $\alpha,\gamma$-di-n-butylamine; dextrin fatty acid esters, such as dextrin palmitic acid ester, dextrin stearic acid ester and dextrin 2-ethylhexanoic acid palmitic acid ester; fatty acid esters of fructoligosaccharides and inulin; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay.

Examples of the ultraviolet absorbents include ultraviolet absorbents of benzoic acid type, such as p-aminobenzoic acid; those of anthranilic acid type, such as methyl anthranilate, those of salicylic acid type, such as methyl salicylate; those of succinic acid type, such as octyl p-methoxysuccinate; those of benzophenone type, such as 2,4-dihydroxybenzophexone; those of urocanic acid type, such as ethyl urocanate; and those of dibenzoylmethane type, such as 4-t-butyl-4'-methoxydibenzoylmethane.

Examples of the moisture retention agent include glycerin, sorbitol, propylene glycol, dipropylene glycol, 1,3-butylene glycol, pentylene glycol, glucose, xylitol, maltitol, polyethylene glycol, hyaluronic acid, chondroitin sulfuric acid, pyrrolidone carboxylate, polyoxyethylene glycoside, and polyoxypropylene methylglycoside.

For the antiseptics, alkyl para-oxybenzoates, benzoic acid, sodium benzoate, sorbic acid, potassium sorbate, and phenoxyethanol may be used. For the antibacterial agents, benzoic acid, salicylic acid, carbolic acid, sorbic acid, para-oxybenzoic acid alkyl esters, para-chloromethacresol, hexachlorophene, benzalkonium chloride, chlorohexydine chloride, trichlorocarbanilide, photosensitizer, and phenoxyethanol.

Examples of the antioxidants include tocopherol, butylhydroxyanisole, dibutylhydroxytoluene and phytic acid; examples of the pH regulators include lactic acid, citric acid, glycolic acid, succinic acid, tartaric acid, dl-malic acid, potassium carbonate, sodium hydrogen carbonate and ammonium hydrogen carbonate; examples of the chelating agents include alanine, sodium ethylenediaminetetraacetate, sodium polyphosphate, sodium metaphosphate and phosphoric acid; examples of the refrigerants include L-menthol and camphor; and examples of the anti-inflammatory agents include allantoin, glycyrrhizin and salts thereof, glycyrrhetinic acid and stearyl glycyrrhetinate, tranexamic acid and azulene.

Examples of the skin-beautifying components include whitening agents, such as placenta extract, arbutin, glutathione and Yukinoshita extract; cell activators, such as royal jelly, photosensitizers, cholesterol derivatives and calf blood extract; rough and dry skin improvers; blood circulation improvers, such as nonylic acid vanillyl amide, benzyl nicotinate, beta-butoxyethyl nicotinate, capsaicin, zingerone, cantharis tincture, ichtammol, caffeine, tannic acid, alpha-borneol, tocopheryl nicotinate, inositol hexanicotinate, cyclandelate, cinnarizine, tolazoline, acetyl choline, verapamil, cepharanthin and gamma-oryzanol; skin astringents, such as zinc oxide and tannic acid; and antiseborrheic agents, such as sulfur and thianthol.

Examples of the vitamins include vitamin A, such as vitamin A oil, retinol, retinyl acetate and retinyl palmitate; vitamin B, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin B15 and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as alpha tocopherol, beta-tocopherol, gamma-tocopherol, dl-alpha-tocopheryl acetate, dl-alpha-tocopheryl nicotinate and dl-alpha-tocopheryl succinate; vitamin H; vitamin P; nicotinic acids, such as nicotinc acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of the amino acids include glycine, valine, leucine, isoleucine, serine, threonine, phenylaranine, alginine, lysine, aspartic acid, glutamic acid, cystine, cysteine, methionine, and tryptophan; examples of the nucleic acids include deoxyribonucleic acid; and examples of the hormones include estradiol and ethenyl estradiol.

The term "cosmetics" as used herein is intended to include skin care products, such as face lotion, milky lotion, cream, face cleansing cream, massage materials, toilet soap and detergent antiperspirant and deodorant; makeup products, such as, foundation, makeup base, rouge, eye shadow, mascara, eyeliner and lipstick; and hairdressing products, such as shampoo, rinse, treatment. Additionally, the present cosmetic materials may have various forms such as liquid, emulsion, solid, paste, gel, and spray.

The present invention will be further explained in detail below by referring to the Examples. However, the present invention shall not be limited to these examples. "%" described below means "% by weight" unless otherwise specified.

EXAMPLES

Preparation Example 1

To a reaction vessel were placed 120 parts by weight of organohydrogen siloxane according to the following formula (4),

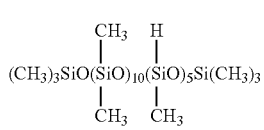

100 parts by weight of ethanol 150 parts by weight of polyether having an allyl group at one end according to the following formula (5),

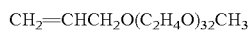

and 38 parts by weight of triethoxyvinyl silane. Then 2 parts by weight of a 0.5 wt. % chloroplatinic acid solution in isopropyl alcohol were added to proceed with reaction for 6 hours under reflux of the solvent.

The reaction mixture was heated under reduced pressure to distill the solvent off to obtain organopolysiloxane according to the following formula (6). The product was a pale brown solid with a melting point of 46 degrees C.

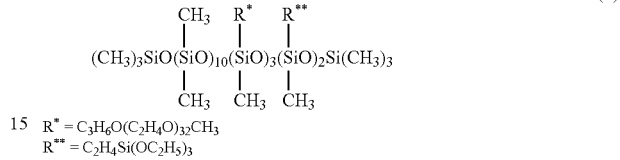

Preparation Example 2

To a reaction vessel were placed 64 parts by weight of organohydrogen siloxane according to the following formula (7),

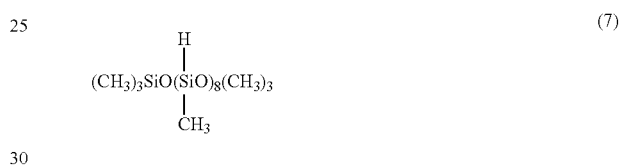

100 parts by weight of ethanol, 300 parts by weight of polyether having an allyl group at one end according to the following formula (8),

and 38 parts by weight of triethoxyvinyl silane. Then, 2 parts by weight of a 0.5 wt. % chloroplatinic acid solution in isopropyl alcohol were added to proceed with reaction for 6 hours under reflux of the solvent.

The reaction mixture was heated under reduced pressure to distill the solvent off to obtain organopolysiloxane according to the following formula (9). The product was a transparent pale-brown liquid with a viscosity of 100 mm$^2$/sec at 25 degrees C.

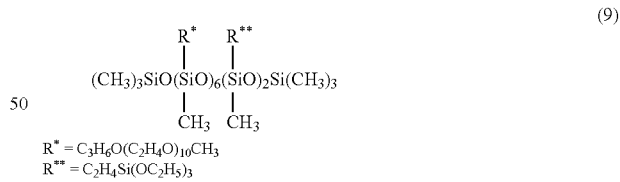

Preparation Example 3

To a reaction vessel were placed 24 parts by weight of cyclotetramethyl siloxane according to the following formula (10),

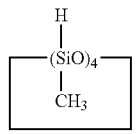

100 parts by weight of ethanol 100 parts by weight of polyether modified with an allyl group at one end according to the following formula (8)

$$CH_2=CHCH_2O(C_2H_4O)_{10}CH_3 \qquad (8)$$

and 38 parts by weight of triethoxyvinyl silane. Then, 2 parts of a 0.5 wt. % chloroplatinic acid solution in isopropyl alcohol were added to proceed with reaction for 6 hours under reflux of the solvent.

The reaction mixture was heated under reduced pressure to distill the solvent off to obtain organopolysiloxane according to the following formula (11). The product was a transparent pale-brown liquid with a viscosity of 45 mm$^2$/sec at 25 degrees C.

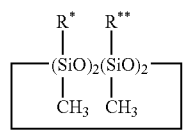

$R^* = C_3H_6O(C_2H_4O)_{10}CH_3$
$R^{**} = C_2H_4Si(OC_2H_5)_3$

Example 1

Five grams of the silicone compound from the above-described Preparation Example 1 were dissolved in ethanol. Then 100 g of titanium dioxide, MT-100SA from Teika, Co., Ltd., was added and dispersed. The solvent was distilled off and the hydrolysis was carried out at 100 degrees C. for 3 hours to obtain a composition of titanium dioxide (A).

Example 2

Five grams of the silicone compound from the above-described Preparation Example 2 were dissolved in ethanol. The, 100 g of titanium dioxide, MT-100SA, from Teika, Co., Ltd., was added and dispersed Then the solvent was distilled off and the hydrolysis was carried out at 100 degrees C. for 3 hours to obtain a composition of titanium dioxide (B).

Example 3

Five grams of the silicone compound from the above-described Preparation Example 3 were dissolved in ethanol. Then 100 g of zinc oxide, MZ-500 from Teika, Co., Ltd., was added and dispersed Then the solvent was distilled off and the hydrolysis was carried out at 100 degrees C. for 3 hours to obtain a composition of zinc oxide (C).

Example 4

Five grams of the silicone compound from the above-described Preparation Example 2 were dissolved in ethanol. Then 100 g of zinc oxide, MZ-500 from Teika, Co., Ltd., was added and dispersed Then the solvent was distilled off and the hydrolysis was carried out at 100 degrees C. for 3 hours to obtain a composition of zinc oxide (D).

Comparative Example 1

Five grams of polyether-modified silicone, KF-6018, were dissolved in ethanol. Then 100 g of titanium dioxide, MT-100SA from Teika, Co., Ltd., was added and dispersed Then the solvent was distilled off and the residue was dried at 100 degrees C. for 3 hours to obtain a composition of titanium dioxide (E).

Example 5

Thirty grams of the composition of titanium dioxide (A) of Example 1, 60 g of water, and 10 g of 1,3-butyleneglycol were mixed and dispersed with the use of a beads mill to obtain a dispersion of titanium dioxide (F).

Example 6

Thirty grams of the composition of titanium dioxide (B) of Example 2, 60 g of water, and 10 g of 1,3-butyleneglycol were mixed and dispersed with the use of a beads mill to obtain a dispersion of titanium dioxide (G).

Example 7

Thirty grams of the composition of zinc oxide (C) of Example 3, 60 g of water, and 10 g of 1,3-butyleneglycol were mixed and dispersed with the use of a beads mill to obtain a dispersion of zinc oxide (H).

Example 8

Thirty grams of the composition of zinc oxide (C) of Example 4, 60 g of water, and 10 g of 1,3-butyleneglycol were mixed and dispersed with the use of a beads mill to obtain a dispersion of zinc oxide (I).

Comparative Example 2

Thirty grams of the composition of titanium dioxide (E) of Comparative Example 1, 60 g of water, and 10 g of 1,3-butyleneglycol were mixed and dispersed with the use of a beads mill to obtain a dispersion of titanium dioxide (J).

Evaluation of Dispersibility

Each sample from the powder compositions and the dispersions of powder obtained in Examples 1 to 8 and Comparative Examples 1 and 2 was mixed in water in a concentration of the powder of 5%, and the mixture was put in a 50 ml tube settler and was allowed to settle for two days. A ratio of a height of the sediment to the total height was determined. The results are as shown in the table below.

In Examples 1 to 8, the dispersions remained homogeneous with little settling observed, and therefore their dispersibility was good. However, in Comparative Examples 1 and 2, the dispersions were inhomogeneous and substantial settling was observed.

|  | Ratio (%) |
| --- | --- |
| Example 1 | 0.3 |
| Example 2 | 0.5 |
| Example 3 | 0.2 |
| Example 4 | 0.4 |
| Example 5 | 0.3 |
| Example 6 | 0.6 |
| Example 7 | 0.5 |
| Example 8 | 0.6 |
| Com. Ex. 1 | 10.5 |
| Com. Ex. 2 | 6.2 |

Examples 9 to 12 and Comparative Example 3

Sunscreen Agent

Sunscreen agents were prepared in the formulation shown in Table 1 to evaluate the product quality. The unit for the numerals in the table is "part by weight".

TABLE 1

|  | Example | | | | Com. Ex. 3 |
|---|---|---|---|---|---|
|  | 9 | 10 | 11 | 12 | 3 |
| 1 Stearic acid | 1.0 | 1.0 | 1.0 | 1.0 | 1.0 |
| 2 Behenyl alcohol | 0.5 | 0.5 | 0.5 | 0.5 | 0.5 |
| 3 Stearic acid monoglyceride | 0.5 | 0.5 | 0.5 | 0.5 | 0.5 |
| 4 Glyceryl triisooctenoate | 15.0 | 15.0 | 15.0 | 15.0 | 15.0 |
| 5 Octyl p-methoxycinnamate | 3.0 | 3.0 | 3.0 | 3.0 | 3.0 |
| 6 Sorbitan sesquioleate | 0.5 | 0.5 | 0.5 | 0.5 | 0.5 |
| 7 Sorbitan POE monooleate | 1.5 | 1.5 | 1.5 | 1.5 | 1.5 |
| 8 1,3-Butylene glycol | 4.0 | 4.0 | 4.0 | 4.0 | 4.0 |
| 9 TEA | 0.6 | 0.6 | 0.6 | 0.6 | 0.6 |
| 10 Carbomer (1% solution) | 15.0 | 15.0 | 15.0 | 15.0 | 15.0 |
| 11 Purified water | Balance | Balance | Balance | Balance | Balance |
| 12 Titanium dioxide dispersion (F) of Ex. 5 | 30 | | | | |
| 13 Titanium dioxide dispersion (G) of Ex. 6 | | 30 | | | |
| 14 Zinc oxide dispersion (H) of Ex. 7 | | | 30 | | |
| 15 Zinc oxide dispersion (I) of Ex. 8 | | | | 30 | |
| 16 Titanium dioxide dispersion (J) of Com. Ex. 2 | | | | | 30 |
| Evaluation Results | | | | | |
| 1. Stability of dispersion | ++ | ++ | ++ | ++ | − |
| 2. User's staisfaction | | | | | |
| Light and smooth touch | ++ | ++ | ++ | ++ | − |
| Spreadability | ++ | ++ | ++ | ++ | + |
| Transparency of cosmetic film | ++ | ++ | ++ | ++ | − |
| Non-stickiness | ++ | ++ | ++ | ++ | − |
| Protecting effect against sun burn | ++ | ++ | ++ | ++ | + |
| Easiness to wash off | ++ | ++ | ++ | ++ | + |

Preparation Procedures of Sunscreen Agent

A: Components 1, 2, 3, 4, and 5 were dissolved under heating.
B: Components 6, 7, 8, 9, and 11 were heated and mixed homogeneously.
C: A was added to B to emulsify
D: Component 10 was added to C. Then components 12 to 16 were added to obtain a sunscreen agent.

The evaluations of the products as described in Table 1 were done according to the following procedures.

1. Stability of the Powder Dispersion

After allowing the sunscreen agents to stand sill at room temperature for a month, the aggregation of powder was observed to determine the stability of the dispersion according to the following criteria.
Evaluation criteria ++: no aggregation is observed.
+: slight aggregation of powder is observed.
−: a tendency to aggregate is observed.
−−: aggregation of powder is clearly observed.

2. Evaluation of the Feeling in Use

The obtained sunscreen agents were evaluated by 50 women panelists using the following criteria for light and smooth touch, spreadability, transparency of cosmetic films, stickiness of skin, sun burn protecting effect, and easiness to wash off.
Criteria for Evaluation

| 5 points | good |
| 4 points | slightly good |
| 3 points | ordinary |
| 2 points | slightly bad |
| 1 point | bad |

The scores were averaged and graded as follows according to the following criteria.
Evaluation of the average point

| 4.5 or higher | ++ |
| not lower than 3.5 and less than 4.5 | + |
| not lower than 2.5 and less than 3.5 | − |
| not lower than 1.5 and less than 2.5 | −− |

As is clear from the results in Table 1, the sunscreen agents of Examples 9 to 12 did not show aggregation and had good dispersibility. The users satisfaction was also good in every item. In contrast in the sunscreen agent of the Comparative Example 3 where the powder was dispersed in polyethersilicone, slight aggregation was observed, the transparency of the cosmetic film was inferior, and the user satisfaction was bad.

Example 13

Suncut Agent

| Component | Weight % |
|---|---|
| 1. Triisododecyl isononanate | 15.0 |
| 2. Octyl para-methoxycinnamate | 5.0 |
| 3. Sepigel 305[1] | 2.5 |
| 4. 1,3-Butylene glycol | 6.0 |
| 5. Purified water | balance |
| 6. Titanium dioxide dispersion (F) of Example 5 | 40.0 |

[1]Emulsifier of polyamide type from SEPIC.

Preparation Procedures

A: Components 1 and 2 were combined.
B: Components 3 to 5 were mixed homogeneously.
C: A was added to B to emulsify. Then component 6 was added to obtain a suncut agent.

The suncut agent thus obtained was found to spread lightly, have a non sticky and non oily touch and to have transparent appearance. It was also washed off very easily.

Example 14

Creamy Lipcolor

| Component | Weight % |
|---|---|
| 1. Dextrin palmitate/ethylhexanoate[1] | 9.0 |
| 2. Glyceryl triisooctanoate | 22.0 |
| 3. Bentonite | 0.7 |
| 4. Polyether-modified siloxane[2] | 1.5 |
| 5. Decamethylcyclopentasiloxane | 42.0 |
| 6. 1,3-Butylene glycol | 4.0 |
| 7. Sodium chloride | 0.5 |
| 8. Purified water | 15.3 |
| 9. Dispersion of titanium dioxide (G) of Example 6 | 5.0 |
| 10. Coloring pigment | q.s. |

[1]Rheopal TT from Chiba Seifun Co., Ltd.
[2]KF6019 from Shin-Etsu Chemical Co., Ltd.

Preparation Procedures

A: Component 1, a part of component 2 and components 3 to 5 were mixed and dissolved.
B: To the rest of component 2 was added component 10 to disperse with rollers.
C: B was added to A to mix homogeneously.
D. Components 6 to 9 were mixed and heated.
E. D was added to C to emulsify.

It was confirmed that the thus obtained W/O type creamy lip color was good in makeup coverage endurance, had a non sticky and non oily touch, and spread lightly.

Example 15

Mascara

| Component | Weight % |
|---|---|
| 1. Polyvinyl alcohol | 15.0 |
| 2. Ethanol | 3.0 |
| 3. Purified water | 57.0 |
| 4. Glyceryl trioctanoate | 2.0 |
| 5. Polyoxyethylenesorbitan oleate (20EO) | 0.5 |
| 6. Ethanol | 8.0 |
| 7. 1,3-Butylene glycol | 1.0 |
| 8. Purified water | 1.0 |
| 9. Antiseptics | q.s. |
| 10. Dispersion of titanium dioxide (B) of Example 2 | 6.0 |
| 11. Bentonite | 1.0 |
| 12. Purified water | balance |

Preparation Procedures

A: Components 1 to 3 were mixed to dissolve under heating. Components 4 to 6 were added and mixed homogeneously.
B: Components 7 to 10 were mixed and dispersed.
C: B was added little by little to A to emulsify and components 11 and 12 were added and mixed homogeneously to obtain a facial pack material.

The facial pack material thus obtained had good dispersibility of pigment, spread lightly, and did not cause quality change with temperature change and time. It showed a good user satisfaction and stability.

Example 16

Eyeshadow

| Component | Weight % |
|---|---|
| 1. Decamethylcyclopentasiloxane | 10.0 |
| 2. Dimethylpolysiloxane (6 mm$^2$/sec at 25 degrees C.) | 10.0 |
| 3. Crosslinked polyether-modified silicone[1] | 7.0 |
| 4. PEG (10) lauryl ehter | 0.5 |
| 5. Silicon treated cromium oxide[2] | 6.2 |
| 6. Ultramarine blue treated with silicone[2] | 4.0 |
| 7. Titanium coated mica treated with silicone[2] | 6.0 |
| 8. Sodium chloride | 2.0 |
| 9. Propylene glycol | 7.0 |
| 10. Antiseptics | q.s. |
| 11. Fragrance | q.s. |
| 12. Purified water | 37.3 |
| 13. Dispersion of titanium dioxide from Experiment 5 (F) | 10.0 |

[1]KSG210 from Shin-Etsu Chemical Co., Ltd.
[2]Silicone treated powder was obtained as follows: 3 parts by weight of a reactive acrylic silicone resin with an ethoxy group, KP 574 from Shin-Etsu Chemical Co., Ltd., and 97 parts by weight of powder were combined and heated.

Preparation Procedures

A: Components 1 to 4 were mixed. Then components 5 to 7 were added and dispersed homogeneously.
B: Components 8 to 10, 12, and 13 were mixed homogeneously.
C. While stirring, B was added little by little to A and to the resulting mixture was added component 11 to obtain eyeshadow.

The eyeshadow thus obtained demonstrated a light spreadability without oily look nor powdery look and gave moisturizing and refreshing feel to users. It also had a good water resistance and a good sweat resistance and makeup coverage lasted long. No quality change was found with temperature change and time.

Example 17

Mascara

| Component | Weight % |
|---|---|
| 1. Stearic acid | 2.0 |
| 2. Carnauba wax | 2.0 |
| 3. White beeswax | 7.0 |
| 4. Polyoxyethylene sorbitan monooleate (20EO) | 0.8 |
| 5. Sorbitan sesquioleate | 0.4 |
| 6. Triethanolamine | 0.5 |
| 7. Fatty acid sugar ester | 1.5 |
| 8. Composition of titanium dioxide (A) of Example 1 | 2.0 |
| 9. Treated iron oxide black[1] | 6.0 |
| 10. Treated mica[2] | 3.0 |
| 11. Propylene glycol | 7.0 |
| 12. Antiseptics | q.s. |
| 13. Emulsion of ethyl polyacrylate | 50.0 |
| 14. Purified water | balance |

[1]97 parts by weight of iron oxide black was treated with 3 parts by weight of organopolysiloxane from Preparation Example 1.
[2]98 parts by weight of mica was treated with 2 part by weight of organopolysiloxane from Preparation Example 1.

Preparation Procedures

A: Components 1 to 7 were mixed under heating.

B: Components 8 to 11 were treated with a three roll will.

C: Components 12 to 14 were added to B and the resulting mixture was heated.

D: C was added A to emulsify. The emulsion was allowed to cool to obtain mascara.

The mascara thus obtained was good in pigment dispersion, spread lightly without oily look nor powdery look and gave a shiny finish. It also had a good water resistance and a good sweat resistance and makeup coverage lasted long. No quality change was found with temperature change and time.

Example 18

Suncut Cream

| Component | Weight % |
| --- | --- |
| 1. Decamethylcyclopentasiloxane | 17.5 |
| 2. Acrylic silicone resin/decamethylcyclopentasiloxane[1] | 12.0 |
| 3. Glyceryl triisooctanoate | 5.0 |
| 4. Octyl pera-methoxycinnamate | 6.0 |
| 5. Crosslinked polyethermodified silicone[2] | 5.0 |
| 6. Branched polyether-modified silicone[3] | 1.0 |
| 7. Hydrophilized zinc oxide | 20.0 |
| 8. Sodium chloride | 0.5 |
| 9. 1,3-Butylene glycol | 2.0 |
| 10. Antiseptics | q.s. |
| 11. Fragrance | q.s. |
| 12. Purified water | 21.0 |
| 13. Dispersion of zinc oxide (H) of Example 7 | 10.0 |

[1]KP545 from Shin-Etau Chemical Co., Ltd.
[2]KSG210 from Shin-Etsu Chemical Co., Ltd.
[3]KF6028 from Shin-Etsu Chemical Co., Ltd.

Preparation Procedures

A: To a part of component 1 was added component 2 to mix homogeneously. Then component 7 was added and dispersed with a beads mill.

B: The rest of component 1 and components 3 to 6 were mixed homogeneously.

C: Components 8 to 10, 12 and 13 were mixed to dissolve homogeneously.

D: C was added to B to emulsify. To the emulsion was added A and component 11 to obtain suncut cream.

The suncut cream thus obtained was non sticky, had a light spreadability, a good adhesion, and a shiny gloss, and well fit toward skin. Makeup coverage maintained long, and it was also found that the present suncut cream did not cause quality change with temperature change and time.

Example 19

Suntan Cream

| Component | Weight % |
| --- | --- |
| 1. Decamethylcyclopentasiloxane | 15.0 |
| 2. Dimethylpolysiloxane (6 mm²/sec at 25 degrees C.) | 5.0 |
| 3. Stearyl-modified acrylic silicone[1] | 0.5 |
| 4. Polyether-modified silicone[2] | 5.0 |
| 5. Palmitic acid | 0.2 |
| 6. Dimethyloctyl para-aminobenzoate | 0.5 |
| 7. 4-t-butyl-4'-methoxy-dibenzoylmethane | 0.5 |
| 8. Kaolin | 0.5 |
| 9. Iron oxide red | 0.2 |
| 10. Iron oxide yellow | 0.3 |
| 11. Iron oxide black | 0.1 |
| 12. Titanium dioxide coated maica | 1.0 |
| 13. Composition of titanium dioxide (A) of Example 1 | 0.5 |
| 14. Sodium glutamate | 3.0 |
| 15. 1,3-Butylene glycol | 5.0 |
| 16. Dioctadecyldimethylammonium chloride | 0.1 |
| 17. Antioxidatn | q.s. |
| 18. Antiseptics | q.s. |
| 19. Fragrance | q.s. |
| 20. Purified water | 62.6 |

[1]KP 561 P from Shin-Etsu Chemical Co., Ltd.
[2]KF 6017 from Shin-Etsu Chemical Co., Ltd.

Preparation Procedures

A: Components 1 to 7, 17, and 18 were dissolved under heating.

B: Component 16 and a part of component 20 were heated with stirring, and then to the resulting mixture were added components 8 to 18 and dispersed.

C: Components 14, 15, and the rest of component 20 were dissolved homogeneously to mix with B D: While stirring, C was added to A to emulsify. The resulting mixture was allowed to cool and then component 19 was added to obtain suntan cream.

The suntan cream thus obtained was found to spread lightly, have a fine texture, a non sticky and non oily touch, provide moisturizing, hydrating and refreshing feel to user and well fit toward skin. It was also found that makeup coverage maintains long. It was also confirmed that the present suntan cream did not cause quality change with temperature change and time, such as separation and aggregation of powder.

Example 20

Suncut Milky Lotion

| Component | Weight % |
| --- | --- |
| 1. Decamethylcyclopentasiloxane | 3.0 |
| 2. Dimethylpolysiloxane (6 mm²/sec at 25 degrees C.) | 5.0 |
| 3. Glyceryl triisooctanoate | 5.0 |
| 4. Polyether-modified silicone[1] | 1.0 |
| 5. Crosslinked polyether-modified silicone[1] | 3.0 |
| 6. Dispersion of titanium dioxide/decamethylcyclopentasiloxane[3] | 25.0 |
| 7. Dispersion of zinc oxide/decamethylcyclopentasiloxane[4] | 35.0 |
| 8. Dipropylene glycol | 2.0 |
| 9. Sodium citrate | 0.5 |
| 10. Antiseptics | q.s. |
| 11. Fragrance | q.s. |
| 12. Purified water | 15.5 |
| 13. Dispersion of titanium dioxide (F) of Example 5 | 5.0 |

[1]KF-6019 from Shin-Etsu Chemical Co., Ltd.
[2]KSG-210 from Shin-Etsu Chemical Co., Ltd.
[3]SPD-T1V from Shin-Etsu Chemical Co., Ltd.
[4]SPD-Z1S from Shin-Etsu Chemical Co., Ltd.

Preparation Procedures

A: Components 1 to 5 were combined and mixed homogeneously.

B. Components 8 to 10, 12, and 13 were mixed and dissolved.

C: B was added to A to emulsify. Then components 6, 7, and 11 were added to obtain suncut milky lotion.

The suncut milky lotion thus obtained was non sticky had a light spreadability, a good adhesion, and a shiny gloss, and well fit toward skin. Makeup coverage maintained long. It was also found that the present foundation did not cause quality change with temperature change and time.

Example 21

Foundation

| Component | Weight % |
| --- | --- |
| 1. Decamethylcyclopentasiloxane | 45.0 |
| 2. Dimethylpolysiloxane (6 mm$^2$/sec at 25 degrees C.) | 3.5 |
| 3. Crosslinked polyether-modified silicone[1] | 3.0 |
| 4. Polyether-modified silicone[2] | 0.5 |
| 5. Dimethyldistearylammonium hectorite | 4.0 |
| 6. Hydrophobized titanium dioxide[3] | 10.0 |
| 7. Hydrophobized talc[3] | 6.0 |
| 8. Hydrophobized mica[3] | 6.0 |
| 9. Hydrophobized iron oxide red[3] | 1.6 |
| 10. Hydrophobized iron oxide yellow[3] | 0.7 |
| 11. Hydrophobized iron oxide black[3] | 0.2 |
| 12. Dipropylene glycol | 4.0 |
| 13. Methyl para-oxybenzoate | 0.3 |
| 14. Methyl 2-amino-2-methyl-1,3-proprandiol | 0.2 |
| 15. Hydrochloric acid | 0.1 |
| 16. Fragrance | q.s. |
| 17. Water | 9.9 |
| 18. Dispersion of titanium dioxide (G) of Example 6 | 5.0 |

[1]KSG-210 from Shin-Etsu Chemical Co., Ltd.
[2]KF-6019 from Shin-Etsu Chemical Co., Ltd.
[3]Hydrophobizing treatment: 2 parts by weight of a reactive branched alkyl silicone-modified silicone with an ethoxy group, KF-9909 from Shin-Etsu Chemical Co., Ltd. were added to 98 parts by weight of powder and heated.

Preparation Procedures

A: Components 1 to 5 were mixed and heated. Then components 6 to 11 were added and mixed homogeneously.

B: Components 12 to 15, 17 and 18 were dissolved with heat while the pH of the aqueous phase was maintained at 9.0.

C: While stirring, B was added to A to emulsify. The emulsion was allowed to cool and component 16 was added to obtain foundation.

The foundation thus obtained was found to spread lightly, have a fine texture, a non sticky and non oily touch, and provide moisturizing, hydrating and refreshing feel to user. It was also found that makeup coverage maintains long and the present foundation does not cause quality change with temperature change and time.

Example 22

Liquid Foundation

| Component | Weight % |
| --- | --- |
| 1. Decemethylcyclopentasiloxane | 16.0 |
| 2. Dimethylpolysiloxane (6 mm$^2$/sec at 25 degrees C.) | 8.0 |
| 3. Octyl para-methoxycinnamate | 3.0 |
| 4. 12-Hydroxystearic acid | 1.0 |
| 5. Polyether-modified silicone[1] | 2.0 |
| 6. Flourine-modified silicone[2] | 5.0 |
| 7. Spherical silicone resin powder[3] | 3.0 |
| 8. Fine powder of titanium dioxide treated with fluorine containing compound[4] | 8.0 |
| 9. Fine powder of mica titanium treated with fluorine containing compound[4] | 1.0 |
| 10. Fine powder of titanium dioxide treated with fluorine containing compound[4] | 5.0 |
| 11. Iron oxide black treated with fluorine containing compound[4] | 0.9 |
| 12. Iron oxide yellow treated with fluorine containing compound[4] | 2.0 |
| 13. Iron oxide black treated with fluorine containing compound[4] | 1.0 |
| 14. Ethanol | 15.0 |
| 15. Glycerin | 2.0 |
| 16. Magnesium sulfate | 1.0 |
| 17. Antiseptics | q.s. |
| 18. Fragrance | q.s. |
| 19. Purified water | 16.1. |
| 20. Dispersion of titanium dioxide (F) of Example 5 | 10.0 |

[1]KF-6019 from Shin-Etsu Chemical Co., Ltd.
[2]FL-5 from Shin-Etsu Chemical Co., Ltd.
[3]KMP590 from Shin-Etsu Chemical Co., Ltd.
[4]Powder coated with 5 parts by weight of a perfluoroalkylethyl phosphate diethanol amine salt per 95 parts by weight of the powder.

Preparation Procedures

A: Components 7 to 13 were mixed homogeneously.

B: Components 1 to 6 were mixed under heating. To the resulting mixture was added A to mix homogeneously.

C: Components 14 to 17, 19, and 20 were heated to 40 degrees C. The resulting mixture was added little by little to B to emulsify and allowed to cool. Further component 18 was added to obtain liquid foundation.

The liquid foundation thus obtained was found to spread lightly and have a non sticky, non oily, cool, and refreshing feel. It was also found that the present liquid foundation did not cause quality change with temperature change and time.

Example 23

Hair Cream

| Component | Weight % |
| --- | --- |
| 1. Decamethylcyclopentasiloxane | 10.0 |
| 2. Methylphenylpolysiloxane | 5.0 |
| 3. Squalane | 4.0 |
| 4. Silicone with network structure[1] | 1.0 |
| 5. Glyceryl dioleate | 2.0 |
| 6. Polyether-modified silicone[2] | 4.0 |
| 7. Sorbitol sodium sulfate | 2.0 |
| 8. Chondoroitin sodium sulfate | 1.0 |
| 9. Hyaluronic acid | 0.5 |
| 10. Propylene glycol | 3.0 |
| 11. Antiseptics | 1.5 |
| 12. Vitamin acetate | 0.1 |
| 13. Antioxidant | q.s. |
| 14. Fragrance | q.s. |

-continued

| Component | Weight % |
|---|---|
| 15. Purified water | 55.9 |
| 16. Dispersion of zinc oxide (H) of Example 7 | 10.0 |

[1] A 50% solution, in D5, of silicone with network structure with a ratio of $[Me_3SiO_{1/2}]/[SiO_2]$ of 0.8.
[2] KF6019 from Shin-Etsu Chemical Co., Ltd.

Preparation Procedures

A: Components from 1 to 6 and from 11 to 13 were mixed under heating.

B: Components from 7 to 10, 15 and 16 were dissolved under heating.

C: While string, B was added little by little to A to emulsify. The emulsion was allowed to cool and then component 14 was added to obtain hair cream.

The hair cream thus obtained demonstrated a light spreadability, a non sticky and non oily touch and left skin feeling moisturized and a refreshed. It also had good water resistance and good sweat resistance and makeup coverage lasted long. No quality change was found with temperature change and time.

Example 24

Hair Cream

| Component | Weight % |
|---|---|
| 1. Decamethylcyclopentasiloxane | 10.0 |
| 2. Methylphenylpolysiloxane | 3.0 |
| 3. Liquid paraffins | 5.0 |
| 4. Stearoxy-modified silicone[1] | 8.0 |
| 5. Branched polyether-modified silicone[2] | 2.0 |
| 6. Spherical powder of organopolysiloxane erastomer[3] | 2.5 |
| 7. Hydrophobized silica[4] | 2.0 |
| 8. Zinc stearate | 2.0 |
| 9. Vitamin E acetate | 3.0 |
| 10. Polyethylene glycol 400 | 1.0 |
| 11. Sodium lactate | 1.0 |
| 12. 1,3-Butylene glycol | 5.0 |
| 13. Titanium dioxide composition (B) of Example 2 | 1.0 |
| 14. Antiseptics | q.s. |
| 15. Fragrance | q.s. |
| 16. Purified water | 54.5 |

[1] KF-7002 from Shin-Etsu Chemical Co., Ltd.
[2] KF6028 from Shin-Etsu Chemical Co., Ltd.
[3] KMP-590 from Shin-Etsu Chemical Co., Ltd.
[4] Aerosil R972 from Japan Aerosil Co., Ltd.

Preparation Procedures

A: Components 1 to 5, 8 and 9 were mixed homogeneously. Then components 6 and 7 were added to disperse homogeneously.

B: Components 10 to 14 and 16 were combined to dissolve.

C: B was added little by little to A to emulsify. The component 15 was added to obtain moisture cream.

The moisture cream thus obtained demonstrated a light spreadability, a non sticky and non oily touch and left skin feeling moisturized and refreshed. No quality change was found with temperature change and time.

Example 25

Hand Cream

| Component | Weight % |
|---|---|
| 1. Decamethylcyclopentasiloxane | 30.0 |
| 2. Liquid paraffin | 10.0 |
| 3. Amino-modified silicone gum (amine equivalent weight 70,000 g/mol) | 15.0 |
| 4. Polyether-modified silicone[1] | 4.0 |
| 5. Distearyldimethylammonium chloride | 0.8 |
| 6. Vitamin E acetate | 0.1 |
| 7. Polyethylene glycol 4000 | 1.0 |
| 8. Glycerin | 10.0 |
| 9. Aluminum magnesium silicate | 1.2 |
| 10. Zinc oxide composition of (C) Example 3 | 0.5 |
| 11. Antiseptics | q.s. |
| 12. Fragrance | q.s. |
| 13. Purified water | 27.4 |

[1] KF6017 from Shin-Etsu Chemical Co., Ltd.

Preparation Procedures

A: Components 1 and 3 were mixed to dissolve under heating. Then components 2, from 4 to 6, and 11 were added under heating.

B: Components 7 to 10 and 13 were mixed under heating.

C: B was added little by little to A to emulsify. Then the mixture was allowed to cool and component 12 was added to obtain hand cream.

Hand cream thus obtained demonstrated a light spreadability and a non sticky and non oily touch. In addition, it was also found that it leaves skin feel moisturized and can protect skin effectively when working with water. High stability with temperature change was confirmed.

Example 26

O/W Cream

| Component | Weight % |
|---|---|
| 1. Acrylic silicone resin/decamethylcyclopentasiloxane[1] | 10.0 |
| 2. Stearyl-modified acrylic silicone resin[2] | 8.0 |
| 3. Cetanol | 1.0 |
| 4. Glyceryl triisostearate | 5.0 |
| 5. Stearic acid | 3.0 |
| 6. Glyceryl monostearate | 1.5 |
| 7. Polyether-modified silicone[3] | 0.7 |
| 8. Sorbitan sesquioleate | 0.5 |
| 9. Polyoxyethylenesorbitan monooleate | 1.0 |
| 10. Sodium hydroxide (1% aqueous solution) | 10.0 |
| 11. 1,3-Butylene glycol | 5.0 |
| 12. Antiseptics | q.s. |
| 13. Fragrance | q.s. |
| 14. Purified water | 44.3 |
| 15. Titanium dioxide dispersion of (G) Example 6 | 10.0 |

[1] KP545 from Shin-Etsu Chemical Co., Ltd.
[2] KP561P from Shin-Etsu Chemical Co., Ltd.
[3] KF6018 from Shin-Etsu Chemical Co., Ltd.

Preparation Procedures

A: Components 1 to 6 were mixed to dissolve under heating.

B: Components 7 to 12 and 14 were combined under heating.

C: B was added to A to emulsify. Then the emulsion was allowed to cool and components 13 and 15 were added to obtain O/W cream.

O/W cream thus obtained was non sticky, had a light spreadability, a good adhesion, and a shiny gloss, and well fit toward skin. Makeup coverage maintained long, and it was also found that the present cream did not cause quality change with temperature change and time.

Example 27

Beauty Liquid

| Component | Weight % |
| --- | --- |
| 1. Decamethylcyclopentasiloxane | 12.0 |
| 2. Glyceryl triisooctanoate | 10.0 |
| 3. Polyether-modified silicone[1] | 2.0 |
| 4. Branched polyglycerin-modified silicone[2] | 0.2 |
| 5. Glycerin | 10.0 |
| 6. Magnesium ascorbate/phosphate | 3.0 |
| 7. Sodium chloride | 2.0 |
| 8. Antiseptics | q.s. |
| 9. Fragrance | q.s. |
| 10. Purified water | 50.8 |
| 11. Titanium dioxide dispersion of (F) Example 5 | 10.0 |

[1] KF6018 from Shin-Etsu Chemical Co., Ltd.
[2] KF6100 from Shin-Etsu Chemical Co., Ltd.

Preparation Procedures
A: Components 1 and 2 were mixed under heating.
B: Components 3 to 8, 10, and 11 were dissolved homogeneously under heating.
C: While stirring, B was added to A to emulsify. Then the emulsion was allowed to cool and component 9 was added to obtain beautifying solution.

The beauty liquid thus obtained had a fine texture with a non sticky touch, spread lightly and left skin feeling moisturized and hydrated. It was also found that the present beautifying solution did not cause quality change with temperature change and time, having a very excellent stability

Example 28

Antiperspirant

| Component | Weight % |
| --- | --- |
| 1. Octamethylcyclopentasiloxane | 16.0 |
| 2. Crosslinked silicone[1] | 10.0 |
| 3. Crosslinked polyether-modified silicone[2] | 5.0 |
| 4. Polyoxyethylenesorbitan monooleate (20E.O.) | 0.5 |
| 5. Aluminum zirconium tetrachloride hydrate glycine salt | 20.0 |
| 6. Water | 43.5 |
| 7. Titanium dioxide dispersion (F) of Example 5 | 5.0 |

[1] KSG-15 from Shin-Etsu Chemical Co., Ltd.
[2] KSG-210 from Shin-Etsu Chemical Co., Ltd.

Preparation Procedures
A: Components 1 to 3 were mixed.
B: Component 4 was dissolved in component 6. Then components 5 and 7 were added.
C: While stirring, B was added little by little to A to emulsify to obtain antiperspirant.

The antiperspirant thus obtained was found to have a non sticky or non greasy feel, spread lightly, leave little white residue, and leave skin feeling refreshed. No quality with temperature change and time was found.

Example 29

Treatment Gel

| Component | Weight % |
| --- | --- |
| 1. Ethanol | 20.0 |
| 2. Polyether-modified silicone[1] | 0.5 |
| 3. Glyceryl triisooctanoate | 3.0 |
| 4. Stearoxy-modified silicone[2] | 2.0 |
| 5. Silicone composite powder[3] | 8.0 |
| 6. Carboxyvinylpolymer (1% aqueous solution) | 20.0 |
| 7. Triethanolamine | 0.2 |
| 8. Antiseptics | q.s. |
| 9. Fragrance | q.s. |
| 10. Purified water | 41.3 |
| 11. Titanium dioxide dispersion (G) of Example 6 | 5.0 |

[1] KF6011 from Shin-Etsu Chemical Co., Ltd.
[2] KF-7002 from Shin-Etsu Chemical Co., Ltd.
[3] KSP-100 from Shin-Etsu Chemical Co., Ltd.

Preparation Procedures
A: Components 1 to 5 were mixed to disperse.
B: Components 6 to 8, and 10 were mixed homogeneously
C: A was added little by little to B. Then components 9 and 11 were added to mix homogeneously.

The treatment gel thus obtained was found to spread lightly, have a non sticky and non oily touch, and leave skin feeling moisturized, hydrated, and refreshed. The treatment gel fits well toward skin. No quality change with temperature change and time was found.

Example 30

Deodorant

| Component | Weight % |
| --- | --- |
| 1. Decamethylcyclopentasiloxane | 12.0 |
| 2. Dimethylpolysiloxane(6 mm$^2$/ sec at 25 degrees C.) | 4.0 |
| 3. Polyether-modified silicone[1] | 1.0 |
| 4. Propylene glycol | 31.0 |
| 5. Triclosan | 0.1 |
| 6. Glycerin | 15.0 |
| 7. Sodium chloride | 0.1 |
| 8. Antiseptics | q.s. |
| 9. Fragrance | q.s. |
| 10. Purified water | 25.8 |
| 11. Zinc oxide dispersion of (H) Example 7 | 10.0 |

Preparation Procedures
A: Component 1 to 3 were mixed.
B: Component 5 was dissolved in 4 and component 6 to 8, 10 and 11 were added and mixed.
C: While stirring A vigorously, B was added to emulsify. Then component 9 was added.
D: Into aerosol can was filled 65 parts of C and 35 parts of blowing agent, a mixture of n-butane, isobutane, and propane, to obtain a deodorant agent.

The deodorant agent thus obtained had a non sticky and dry touch. It did not drop even when used in a high content.

It was also found that the effect lasts long and the present deodorant provides users with a comfortable skin feel.

Example 81

O/W/O Type Milky Lotion

| Component | Weight % |
| --- | --- |
| 1. Crosslinked polyether-modified silicone[1] | 3.0 |
| 2. Polyether-modified silicone[2] | 1.0 |
| 3. Glyceryl triisooctanoate | 14.0 |
| 4. Crosslinked alkyl-modified silicone compound[3] | 5.0 |
| 5. Sucrose monostearate | 3.0 |
| 6. Glycerin | 5.0 |
| 7. 1,3-Butylene glycol | 5.0 |
| 8. Antiseptics | q.s. |
| 9. Purified water | 55.0 |
| 10. Titanium dioxide dispersion of (F) Example 5 | 5.0 |
| 11. Macadamia nut oil | 2.0 |
| 12. Cetyl alcohol | 2.0 |
| 13. Fragrance | q.s. |

[1] KSG-210 from Shin-Etsu Chemical Co., Ltd.
[2] KF6019 from Shin-Etsu Chemical Co., Ltd.
[3] KSG-43 from Shin-Etsu Chemical Co., Ltd.

Preparation Procedures
A: Components 1 to 4 were mixed homogeneously.
B: Components 5 to 10 were mixed homogeneously under heating.
C: Components 11 to 18 were mixed under heating.
D: While stirring B, C was added to B to emulsify. Then the emulsion was allowed to cool.
E: While stirring A, D was added to A to emulsify.

The O/W/O type milky lotion thus obtained was found to spread lightly, have a non sticky and non oily touch, and give transparent finish. The makeup coverage lasted long and no quality change with temperature change and time was found. The user satisfaction and the stability were also very good.

Example 32

O/W/O Type Liquid Foundation

| Component | Weight % |
| --- | --- |
| 1. Crosslinked polyether-modified silicone[1] | 4.0 |
| 2. Polyether-modified silicone[2] | 1.0 |
| 3. Propylene glycol decanoate | 5.0 |
| 4. Isopropyl myristate | 5.0 |
| 5. Pigment | 7.0 |
| 6. Titanium dioxide composition | 2.0 |
| 7. Zinc oxide composition | 1.0 |
| 8. Hydrogenated phospholipid derived from egg yolk | 1.0 |
| 9. Glycerin | 2.0 |
| 10. 1,3-Butylene glycol | 10.0 |
| 11. Antiseptics | q.s. |
| 12. Purified water | 52.0 |
| 13. Squalane | 5.0 |
| 14. Cetyl alcohol | 5.0 |
| 15. Fragrance | q.s. |

[1] KSG-210 from Shin-Etsu Chemical Co., Ltd.
[2] KF6019 from Shin-Etsu Chemical Co., Ltd.

Preparation Procedures
A: Components 1 to 4 were mixed homogeneously.
B: Components 5 to 12 were mixed homogeneously under heating.
C: Components 13 to 16 were mixed under heating.
D: While stirring B, C was added to B to emulsify. The emulsion was allowed to cool.
E: While stirring A, D was added to A to emulsify.

The liquid foundation thus obtained was found to spread lightly, have a non sticky and non oily touch, and give a transparent finish. The makeup coverage lasted long and no quality change with temperature change and time was found. The user satisfaction and the stability were also very good.

Example 33

W/O Type Cream

| Component | Weight % |
| --- | --- |
| 1. Crosslinked polyether-modified silicone[1] | 3.0 |
| 2. Crosslinked dimethylpolysiloxane[2] | 20.0 |
| 3. Crosslinked dimethylpolysiloxane[3] | 7.0 |
| 4. Decamethylcyclopentasiloxane | 15.0 |
| 5. Dimethylpolysiloxane(6 mm$^2$/ sec at 25 degrees C.) | 7.0 |
| 6. Polyether-modified silicone[4] | 3.0 |
| 7. Dimethylstearylammonium hectolite | 2.0 |
| 8. Antiseptics | q.s. |
| 9. Fragrance | q.s. |
| 10. Sodium chloride | 0.1 |
| 11. 1,3-Butylene glycol | 10.0 |
| 12. Purified water | 27.9 |
| 13. Titanium dioxide dispersion of (G) Example 6 | 5.0 |

[1] KSG-210 from Shin-Etsu Chemical Co., Ltd.
[2] KSG15 from Shin-Etsu Chemical Co., Ltd.
[3] KSG16 from Shin-Etsu Chemical Co., Ltd.
[4] KF6017 from Shin-Etsu Chemical Co., Ltd.

Preparation Procedures
A: Components 1 to 7 and 9 were mixed homogeneously.
B: Components 8 and 10 to 13 were mixed.
C: B was added to A to emulsify homogeneously.

The W/O type cream thus obtained was found to spread lightly, have a non sticky and non oily feel and leave skin feeling moisturized. It was also found that the present cream is very stable.

Example 34

W/O Type Rouge

| Component | Weight % |
| --- | --- |
| 1. Acrylic silicone resin/Decamethylcyclopentasiloxane[1] | 10.0 |
| 2. Stearyl-modified acrylic silicone resin[2] | 2.0 |
| 3. Decamethylcyclopentasiloxane | 20.0 |
| 4. Glyceryl triisostearate | 3.0 |
| 5. Dimethylstearylammonium hectolite | 1.5 |
| 6. Polyether-modified silicone[3] | 1.5 |
| 7. Nylon | 3.0 |
| 8. Talc | 5.0 |
| 9. Pigments for rouge | 20.0 |
| 10. Alcohol | 5.0 |
| 11. 1,3-Butylene glycol | 4.0 |
| 12. Antiseptics | q.s. |
| 13. Fragrance | q.s. |
| 14. Purified water | 20.0 |
| 15. Titanium dioxide dispersion (F) of Example 5 | 5.0 |

[1] KP545 from Shin-Etsu Chemical Co., Ltd.
[2] KP561P from Shin-Etsu Chemical Co., Ltd.
[3] KF6019 from Shin-Etsu Chemical Co., Ltd.

Preparation Procedures
A: Components 1 to 6 were mixed to dissolve under heating.
B: Components 7 to 9 and 13 were mixed homogeneously. Then the mixture was blended with A.
C: Components from 10 to 12 and from 14 to 15 were mixed under heating.
D: C was added to B to emulsify.

The W/O type rouge thus obtained was non sticky, had a light spreadability, a good adhesion, and a shiny gloss, and well fit toward skin. Makeup coverage maintained long, and it was also found that the present rouge did not cause quality change with temperature change and time.

Example 35

W/O Type Cream

| Component | Weight % |
| --- | --- |
| 1. Crosslinked alkyl/polyether-modified silicone[1] | 3.0 |
| 2. Crosslinked alkyl-modified silicone compound[2] | 4.0 |
| 3. Liquid paraffins | 13.5 |
| 4. Macadamia nut oil | 5.0 |
| 5. Alkyl/polyether-comodified silicone[3] | 0.5 |
| 6. Silicone composite powder[4] | 3.0 |
| 7. Sodium citrate | 0.2 |
| 8. Propylene glycol | 8.0 |
| 9. Glycine | 3.0 |
| 10. Antiseptics | q.s. |
| 11. Fragrance | q.s. |
| 12. Purified water | 54.8 |
| 13. Zinc oxide dispersion of (I) Example 8 | 5.0 |

[1]KSG-310 from Shin-Etsu Chemical Co., Ltd.
[2]KSG-41 from Shin-Etsu Chemical Co., Ltd.
[3]KF6026 from Shin-Etsu Chemical Co., Ltd.
[4]KSP-100 from Shin-Etsu Chemical Co., Ltd.

Preparation Procedures
A: Components 1 to 6 were mixed homogeneously.
B: Components from 7 to 10 and from 12 to 13 were mixed homogeneously.
C: B was added little by little to A to emulsify. Then component 11 was added to obtain W/O type cream.

The W/O type cream thus obtained was non-sticky and spread lightly. It was also found that the present cream did not cause quality change with temperature change and time.

Example 36

Lacquer Resin Coating

| Component | Weight % |
| --- | --- |
| 1. Aqueous acrylic resin of cold drying type (non-volatile content 41.5%) | 58.5 |
| 2. Butylcellosolve | 1.0 |
| 3. Butylcarbitol | 2.5 |
| 4. Water | 17.0 |
| 5. Titanium dioxide composition of (B) Example 2 | 20.0 |
| 6. Clay minerals | 1.0 |

Preparation Procedures
Component 1 to 6 were combined and dispersed with the aid of beads mill to obtain an aqueous lacquer resin coating of cold drying type. The present coating was good in dispersibility, stability of dispersion and did not cause aggregation or sediment. Therefore it maintained a good stability with time.

Example 37

Aqueous Ink

| Component | Weight % |
| --- | --- |
| 1. Ethylene glycol | 17.0 |
| 2. Iron oxide black composition[1] | 14.0 |
| 3. Johcryl J61J[2] | 2.5 |
| 4. Purified water | 66.5 |

[1]The iron oxide black composition was obtained as follows: 5 g of the silicone compound of the above Preparation Example 1 was dissolved in ethanol, to the solution, 100 g of iron oxide black was added and dispersed, the solvent was distilled off and the residue was subjected to hydrolysis for 3 hours at 100 degrees C.
[2]From Johnson Polymer Co., Ltd.

Preparation Procedures
Component 1 to 4 were combined and dispersed with the aid of beads mill to obtain aqueous ink. The present ink had good dispersibility and good dispersion stability and did not cause aggregation nor sediment. It did not cause mottle, showing good stability with time.

EFFECT OF THE INVENTION

The hydrophilized powder which is surface treated with the siloxane compound represented by the formula (1) and the aqueous dispersion thereof can be used in cosmetics. The cosmetics spread lightly, provide moisturized, hydrated, and refreshed feel as well as long lasting makeup coverage, have a non sticky touch and good stability with temperature change and time. Additionally, inks and coatings comprising the same do not cause sediment with time and have good dispersibility and good dispersion stability.

$$R^1_a R^2_b R^3_c SiO_{(4-a-b-c)/2} \tag{1}$$

The invention claimed is:

1. A hydrophilized powder, wherein the powder is surface treated with a polyether-modified silicone having a weight average molecular weight of from 300 to 100,000 and a hydrolyzable silyl group according to the formula $$R^1_a R^2_b R^3_c SiO_{(4-a-b-c)/2}$$

wherein $0.5 \leq a \leq 2.5$, $0.1 \leq b \leq 1.0$, and $0.01 \leq c \leq 1.0$ and
  $R^1$ may be same with or different from each other and is an organic group selected from the group consisting of $C_{1-30}$ alkyl groups, aryl groups, aralkyl groups, and fluorinated alkyl groups,
  $R^2$ is a polyether group according to the following formula $$-C_d H_{2d} - O - (C_2 H_4 O)_e R^4$$

wherein $R^4$ is a $C_{1-30}$ alkyl group and d and e are integers with $0 \leq d \leq 15$ and $1 \leq e \leq 50$, a content of the polyether moiety $(C_2 H_4 O)_e$ ranging from 50 to 80 weight-% relative to the weight of the polyether-modified silicone, and
  $R^3$ is a silyl group having a hydrolyzable group according to the formula $$-C_d H_{2d} SiR^1_g (OR^5)_{3-g}$$

wherein $R^1$ is as defined above, $R^5$ is a hydrogen atom or a $C_{1-6}$ alkyl group, d is as defined above, and $0 \leq g \leq 2$.

2. The hydrophilized powder according to claim 1, wherein the powder is surface treated with 0.1 part by weight or more of the silicone according to claim 1 relative to 100 parts by weight of the powder.

3. The hydrophilized powder according to claim 1 or 2, wherein the powder is zinc oxide.

4. The hydrophilized powder according to claim 1 or 2, wherein the powder is titanium dioxide.

5. The hydrophilized powder according to claim 1 or 2, wherein the powder is extender such as mica and sericite.

6. A composition comprising the hydrophilized powder according to claim 1 or 2.

7. A cosmetic comprising the composition according to claim 6.

8. A coating composition comprising the composition according to claim 6.

9. An ink composition comprising the composition according to claim 6.

10. An aqueous dispersion comprising (A) a hydrophilized powder, wherein the powder is surface treated with a polyether-modifed silicone having a weight average molecular weight of from 300 to 100,000 and a hydrolyzable silyl group according to the formula $R^1_a R^2_b R^3_c SiO_{(4-a-b-c)/2}$ wherein $0.5 \leq a \leq 2.5$, $0.1 \leq b \leq 1.0$, and $0.01 \leq c \leq 1.0$ and $R^1$ may be same with or different from each other and is an organic group selected from the group consisting of $C_{1-30}$ alkyl groups, aryl groups, aralkyl groups, and fluorinated alkyl groups, $R^2$ is a polyether group according to the following formula $-C_d H_{2d}-O-(C_2H_4O)_e R^4$ wherein $R^4$ is a $C_{1-30}$ alkyl group and d and e are integers with $0 \leq d \leq 15$ and $1 \leq e \leq 50$, a content of the polyether moiety $(C_2H_4O)_e$ ranging from 50 to 80 weight-% relative to the weight of the polyether-modified silicone, and $R^3$ is a silyl group having a hydrolyzable group according to the formula $-C_d H_{2d} SiR^1_g (OR^5)_{3-g}$ wherein $R^1$ is as defined above, $R^5$ is a hydrogen atom or a $C_{1-6}$ alkyl group, d is as defined above, and $0 \leq g \leq 2$, (B) water, and/or (C) a water-soluble oil.

11. A cosmetic comprising the aqueous dispersion according to claim 10.

12. A coating composition comprising the aqueous dispersion according to claim 10.

13. An ink composition comprising the aqueous dispersion according to claim 10.

* * * * *